(12) United States Patent
Matho et al.

(10) Patent No.: US 11,957,825 B2
(45) Date of Patent: Apr. 16, 2024

(54) MODIFIED TNF AS A CAPTURE LIGAND (71) Applicant: IMMUNICOM, INC., San Diego, CA (US)

(72) Inventors: Michael Matho, San Diego, CA (US); Steven F. Josephs, San Diego, CA (US); Annette Marleau, San Diego, CA (US)

(73) Assignee: IMMUNICOM INC., San Diego, CA (US)

( * ) Notice: Subject to any disclaimer, the term of this patent is extended or adjusted under 35 U.S.C. 154(b) by 0 days.

(21) Appl. No.: 17/843,950

(22) Filed: Jun. 17, 2022

(65) Prior Publication Data

US 2022/0409795 A1 Dec. 29, 2022

Related U.S. Application Data

(60) Provisional application No. 63/211,709, filed on Jun. 17, 2021.

(51) Int. Cl.
| | |
|---|---|
| *A61M 1/36* | (2006.01) |
| *A61K 39/39* | (2006.01) |
| *A61K 39/395* | (2006.01) |
| *B01D 15/38* | (2006.01) |
| *C07K 14/525* | (2006.01) |
| *C07K 14/555* | (2006.01) |
| *C07K 14/70* | (2006.01) |

(Continued)

(52) U.S. Cl.
CPC ........... *A61M 1/362* (2014.02); *A61K 39/395* (2013.01); *A61K 39/39516* (2013.01); *A61K 39/39525* (2013.01); *B01D 15/3809* (2013.01); *B01D 15/3828* (2013.01); *C07K 14/525* (2013.01); *C07K 14/555* (2013.01); *C07K 14/70575* (2013.01); *G01N 33/543* (2013.01); *G01N 33/54353* (2013.01); *A61M 1/3496* (2013.01)

(58) Field of Classification Search
CPC ... A61M 1/3496; A61M 1/362; A61K 39/395; A61K 39/39516; A61K 39/39525; B01D 15/3809; B01D 15/3828; C07K 14/525; C07K 14/555; C07K 14/70575; G01N 33/543; G01N 33/54353
See application file for complete search history.

(56) References Cited

U.S. PATENT DOCUMENTS

| | | |
|---|---|---|
| 5,597,899 A | 1/1997 | Banner et al. |
| 8,501,918 B2 | 8/2013 | Howell |

(Continued)

OTHER PUBLICATIONS

Patent Cooperation Treaty, Written Opinion and International Search Report issued PCT/US2022/034099, dated Oct. 12, 2022, pp. 1-14.

(Continued)

*Primary Examiner* — John Kim
(74) *Attorney, Agent, or Firm* — Pillsbury Winthrop Shaw Pittman LLP (57) ABSTRACT

A column is disclosed for removal of sTNF-R2 from a body fluid. The column has a compartment, an inlet coupled to the compartment and configured to receive the body fluid, and a substrate disposed within the compartment. A capture ligand is coupled to the substrate and has a modified sequence with an amino acid substitution in a reference sequence that includes a portion of a natural TNF sequence. The modified sequence has an affinity for the sTNF-R2 that is greater than an affinity of the reference sequence for the sTNF-R2.

21 Claims, 3 Drawing Sheets

Specification includes a Sequence Listing.

(51) Int. Cl.
*C07K 14/705* (2006.01)
*G01N 33/543* (2006.01)
*A61M 1/34* (2006.01)

(56) References Cited

U.S. PATENT DOCUMENTS

| | | |
|---|---|---|
| 2002/0064829 A1 | 5/2002 | Yu et al. |
| 2012/0107330 A1 | 5/2012 | Stoop |
| 2015/0231233 A1 | 8/2015 | Lentz |
| 2016/0340399 A1 | 11/2016 | Amann et al. |
| 2021/0146030 A1 | 5/2021 | Josephs et al. |

OTHER PUBLICATIONS

Abe, Yasuhiro et al., "Fine tuning of receptor-selectivity for tumor necrosis factor—a using a phage display system with one-step competitive panning", Biomaterials, 2011, pp. 5498-5504, vol. 32.
Mukai, Yohei et al., "Solution of the structure of the TNF-TNFR2 complex", Biochemistry, Nov. 16, 2010, pp. 1-11, vol. 3(148), ra83.
Yu, Mingxia et al., "Targeting transmembrane TNF-a suppresses breast cancer growth", Cancer Research, Jun. 21, 2013 (online), Jul. 1, 2013, pp. 4061-4074, vol. 73(13).
Arguello, Olivia et al., "Apoptosis-inducing TNF superfamily ligands for cancer therapy", Cancers, Mar. 27, 2021, pp. 1-22, vol. 13.

Figure 3 scTNF Mutant Ligand Capture Results

☒ sTNF-R1
☒ sTNF-R2

Figure 4

Figure 5
*Enlarged view of "A"*

Schematic of Combinations of Native Sequence and/or Variant Sequence TNF-alpha Monomers Comprising TNF-alpha Polypeptides (Note: variants can comprise any amino acid modifications disclosed in the invention; linkers are optional)

N-terminus     L = linker     C-terminus

A) TNF-Native — L — TNF-Native — L — TNF-Native
B) TNF-Variant — L — TNF-Variant — L — TNF-Variant
C) TNF-Native — L — TNF-Variant — L — TNF-Variant
D) TNF-Native — L — TNF-Variant — L — TNF-Native
E) TNF-Native — L — TNF-Native — L — TNF-Variant
F) TNF-Variant — L — TNF-Native — L — TNF-Native
G) TNF-Variant — L — TNF-Variant — L — TNF-Native
H) TNF-Variant — L — TNF-Native — L — TNF-Variant

*Figure 6*

SEQUENCE LISTING

```
<160> NUMBER OF SEQ ID NOS: 5

<210> SEQ ID NO 1
<211> LENGTH: 233
<212> TYPE: PRT
<213> ORGANISM: Homo sapiens

<400> SEQUENCE: 1

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
                20                  25                  30

Leu Ser Leu Phe Ser Phe Leu Ile Val Ala Gly Ala Thr Thr Leu Phe
            35                  40                  45

Cys Leu Leu His Phe Gly Val Ile Gly Pro Gln Arg Glu Glu Phe Pro
        50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230

<210> SEQ ID NO 2
<211> LENGTH: 154
<212> TYPE: PRT
<213> ORGANISM: Homo sapiens

<400> SEQUENCE: 2

Ser Ser Arg Thr Pro Ser Asp Lys Pro Val Ala His Val Val Ala Asn
1               5                   10                  15

Pro Gln Ala Glu Gly Gln Leu Gln Trp Leu Asn Arg Arg Ala Asn Ala
```

```
                   20                  25                  30
Leu Leu Ala Asn Gly Val Glu Leu Arg Asp Asn Gln Leu Val Val Pro
            35                  40                  45

Ser Glu Gly Leu Tyr Leu Ile Tyr Ser Gln Val Leu Phe Lys Gly Gln
        50                  55                  60

Gly Cys Pro Ser Thr His Val Leu Leu Thr His Thr Ile Ser Arg Ile
65                  70                  75                  80

Ala Val Ser Tyr Gln Thr Lys Val Asn Leu Leu Ser Ala Ile Lys Ser
                85                  90                  95

Pro Cys Gln Arg Glu Thr Pro Glu Gly Ala Glu Ala Lys Pro Trp Tyr
            100                 105                 110

Glu Pro Ile Tyr Leu Gly Gly Val Phe Gln Leu Glu Lys Gly Asp Arg
        115                 120                 125

Leu Ser Ala Glu Ile Asn Arg Pro Asp Tyr Leu Asp Phe Ala Glu Ser
    130                 135                 140

Gly Gln Val Tyr Phe Gly Ile Ile Ala Leu
145                 150

<210> SEQ ID NO 3
<211> LENGTH: 154
<212> TYPE: PRT
<213> ORGANISM: Artificial Sequence
<220> FEATURE:
<223> OTHER INFORMATION: Synthetic Construct

<400> SEQUENCE: 3

Ser Ser Arg Thr Pro Ser Asp Lys Pro Val Ala His Val Val Ala Asn
1               5                   10                  15

Pro Gln Ala Glu Gly Gln Leu Gln Trp Val Asn Arg Arg Ala Asn Ala
            20                  25                  30

Leu Leu Ala Asn Gly Val Glu Leu Arg Asp Asn Gln Leu Val Val Pro
        35                  40                  45

Ser Glu Gly Leu Tyr Leu Ile Tyr Ser Gln Val Leu Phe Lys Gly Gln
    50                  55                  60

Gly Cys Pro Ser Thr His Val Leu Leu Thr His Thr Ile Ser Arg Ile
65                  70                  75                  80

Ala Val Ser Tyr Gln Thr Lys Val Asn Leu Leu Ser Ala Ile Lys Ser
                85                  90                  95

Pro Cys Gln Arg Glu Thr Pro Glu Gly Ala Glu Ala Lys Pro Trp Tyr
            100                 105                 110

Glu Pro Ile Tyr Leu Gly Gly Val Phe Gln Leu Glu Lys Gly Asp Arg
        115                 120                 125

Leu Ser Ala Glu Ile Asn Arg Pro Asp Tyr Leu Asp Phe Asp Asp Asp
    130                 135                 140

Gly Gln Val Tyr Phe Gly Ile Ile Ala Leu
145                 150

<210> SEQ ID NO 4
<211> LENGTH: 4
<212> TYPE: PRT
<213> ORGANISM: Artificial Sequence
<220> FEATURE:
<223> OTHER INFORMATION: Synthetic Construct

<400> SEQUENCE: 4

Gly Gly Gly Ser
1
```

```
<210> SEQ ID NO 5
<211> LENGTH: 520
<212> TYPE: PRT
<213> ORGANISM: Artificial Sequence
<220> FEATURE:
<223> OTHER INFORMATION: Synthetic Construct

<400> SEQUENCE: 5
```

Thr His His His His His His His His His Ala Gly Gly Ala Glu
1               5                   10                  15

Asn Leu Tyr Phe Gln Gly Ser Ala Ser Ser Ser Arg Thr Pro Ser
            20                  25                  30

Asp Lys Pro Val Ala His Val Val Ala Asn Pro Gln Ala Glu Gly Gln
        35                  40                  45

Leu Gln Trp Val Asn Arg Arg Ala Asn Ala Leu Leu Ala Asn Gly Val
    50                  55                  60

Glu Leu Arg Asp Asn Gln Leu Val Val Pro Ser Glu Gly Leu Tyr Leu
65                  70                  75                  80

Ile Tyr Ser Gln Val Leu Phe Lys Gly Gln Gly Cys Pro Ser Thr His
                85                  90                  95

Val Leu Leu Thr His Thr Ile Ser Arg Ile Ala Val Ser Tyr Gln Thr
            100                 105                 110

Lys Val Asn Leu Leu Ser Ala Ile Lys Ser Pro Cys Gln Arg Glu Thr
        115                 120                 125

Pro Glu Gly Ala Glu Ala Lys Pro Trp Tyr Glu Pro Ile Tyr Leu Gly
    130                 135                 140

Gly Val Phe Gln Leu Glu Lys Gly Asp Arg Leu Ser Ala Glu Ile Asn
145                 150                 155                 160

Arg Pro Asp Tyr Leu Asp Phe Asp Asp Gly Gln Val Tyr Phe Gly
                165                 170                 175

Ile Ile Ala Leu Gly Gly Gly Ser Gly Gly Gly Ser Gly Gly Gly Ser
            180                 185                 190

Gly Gly Gly Ser Ser Ser Arg Thr Pro Ser Asp Lys Pro Val Ala His
        195                 200                 205

Val Val Ala Asn Pro Gln Ala Glu Gly Gln Leu Gln Trp Val Asn Arg
    210                 215                 220

Arg Ala Asn Ala Leu Leu Ala Asn Gly Val Glu Leu Arg Asp Asn Gln
225                 230                 235                 240

Leu Val Val Pro Ser Glu Gly Leu Tyr Leu Ile Tyr Ser Gln Val Leu
                245                 250                 255

Phe Lys Gly Gln Gly Cys Pro Ser Thr His Val Leu Leu Thr His Thr
            260                 265                 270

Ile Ser Arg Ile Ala Val Ser Tyr Gln Thr Lys Val Asn Leu Leu Ser
        275                 280                 285

Ala Ile Lys Ser Pro Cys Gln Arg Glu Thr Pro Glu Gly Ala Glu Ala
    290                 295                 300

Lys Pro Trp Tyr Glu Pro Ile Tyr Leu Gly Gly Val Phe Gln Leu Glu
305                 310                 315                 320

Lys Gly Asp Arg Leu Ser Ala Glu Ile Asn Arg Pro Asp Tyr Leu Asp
                325                 330                 335

Phe Asp Asp Asp Gly Gln Val Tyr Phe Gly Ile Ile Ala Leu Gly Gly
            340                 345                 350

Gly Ser Gly Gly Gly Ser Gly Gly Gly Ser Gly Gly Gly Ser Ser Ser
        355                 360                 365

-continued

```
Arg Thr Pro Ser Asp Lys Pro Val Ala His Val Val Ala Asn Pro Gln
    370             375             380
Ala Glu Gly Gln Leu Gln Trp Val Asn Arg Arg Ala Asn Ala Leu Leu
385             390             395             400
Ala Asn Gly Val Glu Leu Arg Asp Asn Gln Leu Val Val Pro Ser Glu
            405             410             415
Gly Leu Tyr Leu Ile Tyr Ser Gln Val Leu Phe Lys Gly Gln Gly Cys
            420             425             430
Pro Ser Thr His Val Leu Leu Thr His Thr Ile Ser Arg Ile Ala Val
            435             440             445
Ser Tyr Gln Thr Lys Val Asn Leu Leu Ser Ala Ile Lys Ser Pro Cys
    450             455             460
Gln Arg Glu Thr Pro Glu Gly Ala Glu Ala Lys Pro Trp Tyr Glu Pro
465             470             475             480
Ile Tyr Leu Gly Gly Val Phe Gln Leu Glu Lys Gly Asp Arg Leu Ser
            485             490             495
Ala Glu Ile Asn Arg Pro Asp Tyr Leu Asp Phe Asp Asp Asp Gly Gln
            500             505             510
Val Tyr Phe Gly Ile Ile Ala Leu
    515             520
```

MODIFIED TNF AS A CAPTURE LIGAND

CROSS-REFERENCE TO RELATED APPLICATIONS

The present application claims priority to U.S. Provisional Application No. 63/211,709 filed on Jun. 17, 2021, which is hereby incorporated herein in its entirety.

SEQUENCE LISTING

The present application is being filed with a Sequence Listing. The Sequence Listing is submitted electronically in ASCII format via EFS-Web in the form of a text file. Said ASCII copy, created on Jun. 17, 2022, is named "022947-0566243 Sequence_listing_ST25.txt" and is 9.54 KB in size, the contents of which are incorporated herein by reference in their entirety.

BACKGROUND

Apheresis is a medical technology in which the blood of a patient is passed through an apparatus that separates out one or more particular constituents and returns the remainder to the circulatory system. It is thus an extracorporeal therapy. This technology is commonly used to collect platelets at blood donation centers.

The body's control of inflammation and cellular apoptosis is a complex process that is managed by a multitude of regulatory proteins. Tumor necrosis factor alpha (TNF) is a potent cytokine that has been characterized as an anti-tumor agent. Crystallographic studies of TNF show that this cytokine forms homotrimers in vivo to facilitate interactions with TNF receptors. TNF receptors 1 and 2 (TNF-R1 and TNF-R2) that exist as membrane-anchored receptors on cells, through which signaling into the cells occurs upon TNF binding. The transmembrane forms of the TNF receptors are also cleaved from the cell surface, generating soluble forms of the TNF receptors (sTNF-R1 and sTNF-R2) that modulate the activity of TNF by binding to and sequestering this cytokine.

SUMMARY

There is a need for therapeutic approaches for effective and simultaneous removal of one or both of sTNF-R1 and sTNF-R2 using an extracorporeal therapeutic approach in order to augment the activity of TNF in diseases such as cancer. The present disclosure describes systems and methods for the removal of one or both of sTNF-R1 and sTNF-R2 from a blood component.

A column is disclosed for removal of sTNF-R2 from a body fluid. The column has a compartment, an inlet coupled to the compartment and configured to receive the body fluid, and a substrate disposed within the compartment. A capture ligand is coupled to the substrate and has a modified sequence with an amino acid substitution in a reference sequence that includes a portion of a natural TNF sequence. The modified sequence has an affinity for the sTNF-R2 that is greater than an affinity of the reference sequence for the sTNF-R2.

In certain embodiments, the modified sequence comprises an amino acid substituted at a site selected from a group consisting of sites 105, 221, 222, and 223 of SEQ1 (SEQ ID NO:1). In certain embodiments, the amino acid being substituted is selected from a group consisting of aspartic acid (D), glycine (G), histidine (H), asparagine (N), glutamine (Q), serine (S), threonine (T), and valine (V). In certain embodiments, the modified sequence comprises a substitution of D at one or more of sites 221, 222, and 223 of the reference sequence. In certain embodiments, the modified sequence comprises a substitution of D at two or more of sites 221, 222, and 223. In certain embodiments, the modified sequence comprises a substitution of D at all of sites 221, 222, and 223. In certain embodiments, the modified sequence comprises SEQ3 (SEQ ID NO:3).

In certain embodiments, the capture ligand comprises at least two modified sequences. In certain embodiments, the capture ligand comprises a trimer of the modified sequence. In certain embodiments, the capture ligand comprises SEQ11 (SEQ ID NO:5).

In certain embodiments, the capture ligand comprises a linker between the at least two modified sequences. In certain embodiments, the capture ligand does not comprise a linker.

In certain embodiments, the capture ligand further comprises the reference sequence. In certain embodiments, the capture ligand comprises a first trimer of the modified sequence and a second trimer of the reference sequence, each of the first and second trimers coupled separately to the substrate. In certain embodiments, the capture ligand comprises a trimer comprising at least one of the modified sequence and at least one of the reference sequence.

In certain embodiments, the modified sequence has an identity of 95% or greater, 98% or greater with the reference sequence. In certain embodiments, the modified sequence has an identity of 99.9% or less with the reference sequence.

In certain embodiments, the column has a capture efficiency for the sTNF-R2 that is greater than 80% or greater than 90% after 60 minutes of continuous operation at a flow rate of two column volumes per minute.

In certain embodiments, the modified sequence has a $K_D$ that is at least 30% less or at least 100% less than a $K_D$ of the reference sequence.

A method is disclosed for removal of a sTNF-R2 from a body fluid. The method includes the step of passing the body fluid through a compartment containing a substrate coupled to a capture ligand that comprises a modified sequence comprising an amino acid substitution in a reference sequence that comprises a portion of a natural TNF sequence. The modified sequence has an affinity for the sTNF-R2 that is greater than an affinity of the reference sequence for the sTNF-R2.

DETAILED DESCRIPTION

The following description discloses embodiments of ligands, apheresis columns, and methods of extracorporeal therapy for the removal of soluble TNF receptors from blood or a blood component. In certain embodiments, a column is used in conjunction with an apheresis machine.

A typical machine extracts whole blood from a patient and separates the blood into blood components, for example red blood cells, platelets and white cells, and plasma. One of the blood components, for example the plasma, is passed through the column to remove a target material. The processed blood component and the remaining blood components then are integrated and reintroduced into the bloodstream of the patient. Examples of commercially available apheresis machines include a Terumo BCT Spectra Optia System as well as machines made by Fresenius, Haemonetics, Baxter, Nigale and Asahi.

In the context of this disclosure, an apheresis machine may facilitate intravenous removal of blood from a patient and then separation of the blood from said patient into plasma and cell fractions (e.g., using centrifugal forces, a membrane filter, and/or other components). The plasma fraction, or other body fluid, is treated by being pumped through a system as disclosed herein where the plasma passes through a capture support (that includes a substrate with a capture ligand as described herein) that selectively captures a component of the plasma. The plasma is then recombined with the separated cells of the patient and reintroduced into the circulatory system of the patient.

The use of a disclosed system is desirable for application in therapeutic areas where activation of the immune system is desired. An example intent is eliciting signaling by the molecule TNF, which may induce inflammation, trigger cellular apoptosis, cause cellular proliferation, or modify other biological pathways. In general, the disclosed systems and methods are useful for the treatment of cancer, particularly for solid tumors or hematologic malignancies, as well as treatment of infectious diseases, metabolic diseases, hyperproliferative disorders, autoimmune diseases, degenerative diseases, and other disorders associated with immune system dysregulation.

The soluble receptors, sTNF-R1 and sTNF-R2, are produced by different subsets of immune cells and are cleaved from cell surfaces by proteolytic processing, which separates the extracellular domain from the transmembrane and intracellular domains of the receptors. In a healthy human patient, blood plasma levels of sTNF-R2 are generally higher than the levels of sTNF-R1. In certain circumstances, it is desirable to remove different amounts of sTNF-R1 and sTNF-R2 as a treatment.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. It will be apparent to those skilled in the art that the subject technology may be practiced without certain specific details. In some instances, well-known structures and components are shown in block diagram form to avoid obscuring the concepts of the subject technology. Like, or substantially similar, components are labeled with identical element numbers for ease of understanding.

As used within this disclosure, the term "patient" means any organism having a circulatory system. A patient may be a human being. A patient may also be an animal such as a dog or cat or another mammal.

As used within this disclosure, the phrases "body fluid" and "blood component" are used interchangeably to mean one of the fluids into which blood may be separated, for example by centrifugation. For example, blood can be separated into a first blood component that is primarily red cells, a second blood component that is primarily platelets and white cells, and a body fluid that is primarily plasma.

As used within this disclosure, the term "column" and phrase "apheresis column" are used interchangeably and mean a device through which a body fluid from a patient is passed. The column has an internal compartment that contains capture support comprising a substrate on which a capture ligand, which interacts with the body fluid is immobilized. A column may be of various configurations in size and shape and comprise one or more substrates or ligands.

As used within this disclosure, the terms "substrate" and "support" are used interchangeably to mean an object that provides structure while not necessarily interacting with material proximate to the substrate. A substrate or surface of a substrate may comprise one or more organic materials, such as a polysaccharide, and also may comprise one or more inorganic materials, such as metal, plastic, ceramic, or water. A substrate may comprise a portion that has been converted to a different form, for example an oxide, by exposure to a substance, treatment, and/or environment. A substrate may comprise one or more layers, for example a coating or plating.

As used within this disclosure, the term "bead" is used to describe an exemplary structural embodiment of a substrate without excluding other geometric shapes or structures. A bead may be a solid form, such as a solid sphere, or have structure, such as a hollow element or an open-cell foam. A bead may comprise a simple geometric form, for example a sphere or rod, or a more complex form. A bead may comprise a ball, a plate, or a membrane. In an embodiment having internal structure, for example an open-cell foam where a single instance may fill a volume, the diameter may be the average width of passages through the foam. In an embodiment having a complex structure, for example multi-arm stars, the diameter may be the average center-to-center separation of instances of the structure when piled on top of one another.

In certain embodiments, a bead comprises an approximate sphere having a mean, average or absolute diameter in a range of about 1-600 µm. In certain embodiments, a bead has a mean, average or absolute diameter in a range of about 45-165 µm or in a range of about 60-200 µm. A bead can be porous or non-porous. In some embodiments, a bead is porous and comprises pores having a mean, average or absolute diameter in a range of about 10 nm to 100 nm. In certain embodiments, a bead comprises cellulose (e.g., agarose), xylan, dextran, pullulan, starch, the like or a combination thereof. In certain embodiments, a bead is a Sepharose™ particle. In certain embodiments, a surface of the substrate, prior to attachment of a ligand, comprises a reactive carbon. In certain embodiments, the substrate surface comprises a polysaccharide, a cross-linked polysaccharide, an oxidized polysaccharide, a neutral or charged polysaccharide, a reactive carbon, or an aldehyde moiety.

In certain embodiments, the substrate surface is modified to contain chemically active linking groups that can interact with ligand molecules to form stable chemical bonds. An example of this is a surface activation by exposing said substrate surface to sodium meta periodate which results in the formation of formyl groups that can participate in a reductive amination process with amine containing ligands.

As used within this disclosure, the term "target" and phrase "target component" means a chemical, compound, and/or organic structure with which a capture ligand is intended to interact, for example by binding of the ligand to the target. In particular, a target component may be an organic structure, for example a protein, that is desired to be removed from a body fluid.

As used within this disclosure, the term "ligand" means a material that comprising one or more elements having a binding affinity for the target component. In some embodiments, a ligand comprises a binding site that will substantially bind only to specific sites on a target component.

As used within this disclosure, the term "monomer" is to be understood as the smallest protein unit or polypeptide unit present within an oligomeric protein. Reference to a monomer includes a composition consisting of an entire disclosed amino acid sequence and/or a portion of the sequence that includes an active binding site for a target.

As used within this disclosure, a "fragment" or "a functional fragment" is to be understood to refer to both a fragment of a monomer and/or a fragment of a polypeptide or protein. These can be shortened amino acid sequences of a monomer, protein, or polypeptide.

As used within this disclosure, the terms "modified" and "variant" interchangeably refer to a protein, a peptide, a monomer, a polypeptide, or a fragment of one of these entities that comprises an amino acid sequence difference relative to a natural physiological sequence, also referred to herein interchangeably as "natural" and "native." The sequence differences may comprise one or more insertions, deletions or substitutions.

As used within this disclosure, the term "trimer" refers to three protein units, polypeptides or monomers that are associated with one another due to interactions, e.g., hydrophobic interactions, hydrogen bonds, covalent bonds, and/or inclusion of structural motifs that bring about the association of monomers. In this disclosure, a single strand comprising linked TNF monomers may be referred to as a "polypeptide."

As used within this disclosure, the terms "TNF," "TNFa," "TNFα," "TNF-α," "TNF molecule" and variants thereof are used interchangeably and mean a tumor necrosis factor molecule, including entire TNF sequences and partial TNF sequences of natural TNF or modified TNF, and, unless explicitly stated otherwise, include polypeptides comprising one or more entire or partial sequences of one or both of natural TNF and modified TNF.

As used within this disclosure, the phrases "single chain TNF" and "scTNF" and variants thereof refer to a TNF polypeptide that comprise at least two TNF molecules, which may be native TNF sequence or variant TNF sequence, that are stably covalently linked.

As used within this disclosure, the term "homotrimer" refers to a protein or molecule that is comprised of three monomers having identical amino acid sequences.

As used within this disclosure, the term "heterotrimer" refers to a protein or molecule comprising three units of a monomer, wherein at least one of the three monomers exhibits differences in its amino acid sequence from the sequences of other monomers.

As used within this disclosure, the phrase "functional equivalent" refers to a molecule that is modified or varies structurally from a disclosed molecule yet provides the same stated functionality as the disclosed molecule. In certain embodiments, "functional equivalent" refers to a modification to a molecule that does not affect the attachment of the molecule to a target component.

As used within this disclosure, the phrase "linker" or "linking element" means a compound or structure that couples between two different structures, (e.g., between a ligand and a substrate (for example, a surface or a bead) or between two or more monomers within a ligand. A linker can be a chemical bond, amino acid or linear carbon chain. In a preferred embodiment, a linker comprises a peptide. In certain embodiments, a peptide linker consists of between 2 and 30 amino acids, and preferably, between 4 and 20 amino acids. In certain embodiments, a disclosed peptide linker is rich in glycine (i.e., the peptide linker has a high proportion of amino acids that comprise glycine, preferably at least 50% of the amino acids are glycine, and more preferably at least 80% of the amino acids are glycine). In certain embodiments, a peptide linker comprises glycine and serine structures. In certain embodiments, a linker is used to stabilize monomers of a polypeptide strand. In certain embodiments, the formation of a trimeric polypeptide is enhanced by one or more peptide linkers.

As used within this disclosure, the phrases "specifically binds" and "binds specifically" refer to a ligand that binds to a target component in preference to binding other molecules or other peptides as determined by, for example, a suitable in vitro assay (e.g., an Elisa, Immunoblot, and Flow cytometry). A specific binding discriminates over non-specific binding by about 2-fold or more, about 10-fold or more, about 100-fold or more, 1000-fold or more, 10,000-fold or more, 100,000-fold or more, or 1,000,000-fold or more.

As used within this disclosure, the phrase "capture efficiency" refers to the percentage or amount of a target component that is removed from a fluid during a single pass of the fluid through a column. In the context of this disclosure, capture efficiency of a column is determined by the formula $(1-x/y)*100$ where y is the concentration (e.g., pg/ml) of the target in the fluid that enters the column and x is the concentration of the target in the fluid leaving the column and the capture efficiency is expressed as a percentage. In certain embodiments, the units of x and y are a molar concentration.

As used within this disclosure, the term "leaching" means the loss or separation (e.g., dissociation) of a ligand, or portion thereof, from a substrate while a fluid is being passed through the column. As used within this disclosure, a leaching rate is the amount of ligand that dissociates from a substrate over a period of time.

As used within this disclosure, the term "column volume" refers to a volume of a fluid that passes through a column that is approximately equivalent to the volume of the column itself. For example, for a column comprising a 15 ml bead bed, one column volume of a fluid would be equivalent to approximately 15 ml.

As used within this disclosure, the term "patient plasma volume" refers to a volume of a fluid that is approximately equivalent to the total amount of blood in an average healthy patient.

As used within this disclosure, the term "toxic" means that the fluid passing out a column's outlet contains an amount of a substance that is considered to present an unacceptable risk to the patient.

As used within this disclosure, the term "identity" means the amount, usually expressed as a percentage, of amino acid residues that are identical in two sequences.

Natural TNF

TNF signaling occurs through two receptors: TNF-R1 and TNF-R2. TNF exists as a transmembrane form (mTNF) and as a soluble form (sTNF) in the blood. TNF-R1 is expressed on most tissues and can bind to both sTNF and mTNF. TNF-R2 is found typically on cells of the immune system and responds to mTNF. Soluble TNF receptors that bind to either sTNF or mTNF block signaling of that TNF molecule, effectively inactivating the TNF. Elevated levels of sTNF-R1 and/or sTNF-R2 have been observed in association with the presence of cancer in the patient and are believed to be induced by the cancer in order to reduce activation of the immune system.

Disclosed are systems and methods for the selective removal of the soluble forms of TNF receptors that are present in a patient without affecting membrane-bound TNF receptors. The systems and methods disclosed herein are useful for improving an immune response in a patient by increasing the activity and/or the bioavailability of TNF, a cytokine that elicits destruction of tumor cells and/or of tumor vasculature.

The structure of proteins is discussed herein as sequences of amino acids. The amino acid 1-letter codes are listed in Table 1.

TABLE 1

Amino Acid 1-letter Codes

| Amino Acid | 3-Letter Code | 1-Letter Code |
|---|---|---|
| Alanine | Ala | A |
| Cysteine | Cys | C |
| Aspartic acid or aspartate | Asp | D |
| Glutamic acid or glutamate | Glu | E |
| Phenylalanine | Phe | F |
| Glycine | Gly | G |
| Histidine | His | H |
| Isoleucine | Ile | I |
| Lysine | Lys | K |
| Leucine | Leu | L |
| Methionine | Met | M |
| Asparagine | Asn | N |
| Proline | Pro | P |
| Glutamine | Gln | Q |
| Arginine | Arg | R |
| Serine | Ser | S |
| Threonine | Thr | T |
| Valine | Val | V |
| Tryptophan | Trp | W |
| Tyrosine | Tyr | Y |

Table 2 (SEQ1) is a first reference sequence of a natural TNF from www.uniprot.org/uniprot/P01375.

TABLE 2

SEQ1 natural TNF sequence

```
1          11         21         31         41
MSTESMIRDV ELAEEALPKK TGGPQGSRRC LFLSLFSFLI VAGATTLFCL 51         61         71         81         91
LHFGVIGPQR EEFPRDLSLI SPLAQAVRSS SRTPSDKPVA HVVANPQAEG 101        111        121        131        141
QLQWLNRRAN ALLANGVELR DNQLVVPSEG LYLIYSQVLF KGQGCPSTHV 151        161        171        181        191
LLTHTISRIA VSYQTKVNLL SAIKSPCQRE TPEGAEAKPW YEPIYLGGVF 201        211        221        231
QLEKGDRLSA EINRPDYLDF AESGQVYFGI IAL (SEQ ID NO: 1)
```

Table 3 (SEQ2 (SEQ ID NO:2)) is an exemplary second reference sequence of a partial natural TNF.

TABLE 3

SEQ2 partial natural TNF sequence.

```
                                  81         91
                                S SRTPSDKPVA HVVANPQAEG 101        111        121        131        141
QLQWLNRRAN ALLANGVELR DNQLVVPSEG LYLIYSQVLF KGQGCPSTHV 151        161        171        181        191
LLTHTISRIA VSYQTKVNLL SAIKSPCQRE TPEGAEAKPW YEPIYLGGVE 201        211        221        231
QLEKGDRLSA EINRPDYLDF AESGQVYFGI IAL (SEQ ID NO: 2)
```

Modified TNF

In certain embodiments, a protein, peptide, monomer, or polypeptide may be modified by a conservative amino acid substitution. In certain embodiments, a conservative amino acid substitution involves the exchange of an amino acid with a particular type of side chain for an amino acid from the same class. For example, an amino acid with a polar side chain is replaced by another amino acid with a polar side chain. In another example, a first amino acid with a hydrophobic side chain is replaced by a second amino acid with a hydrophobic side chain. In certain embodiments, the identity between a modified sequence and a natural sequence is at least 60%, at least 70%, at least 80%, at least 90%, preferably at least 95%, more preferably at least 97%, or most preferably at least 98%.

A modification of a TNF molecule as disclosed herein may be performed for improving its binding affinity to either sTNF-R1 or sTNF-R2 over the natural TNF molecule. In certain embodiments, the natural TNF has been modified to increase its affinity for TNF-R2. Table 4 lists exemplary sequence variants of a TNF molecule.

TABLE 4

TNF sequence variations

| | Residue position | | | |
|---|---|---|---|---|
| Clone | 105 | 221 | 222 | 223 |
| TNF Ref | L | A | E | S |
| SEQ3 | V | D | D | D |
| SEQ4 | L | H | E | D |
| SEQ5 | L | N | D | D |
| SEQ6 | L | T | S | D |
| SEQ7 | L | Q | D | D |
| SEQ8 | L | T | D | D |
| SEQ9 | L | D | G | D |
| SEQ10 | L | D | E | D |

Table 5 compared an exemplary modified sequence SEQ3 to a reference sequence (SEQ1) of natural TNF.

TABLE 5 comparison of SEQ3 to Reference sequence

```
                                        81         91
REF                                   S SRTPSDKPVA HVVANPQAEG
SEQ3                                  S SRTPSDKPVA HVVANPQAEG 101        111        121        131        141
REF  QLQWLNRRAN ALLANGVELR DNQLVVPSEG LYLIYSQVLF KGQGCPSTHV
SEQ3 QLQWVNRRAN ALLANGVELR DNQLVVPSEG LYLIYSQVLF KGQGCPSTHV 151        161        171        181        191
REF  LLTHTISRIA VSYQTKVNLL SAIKSPCQRE TPEGAEAKPW YEPIYLGGVF
SEQ3 LLTHTISRIA VSYQTKVNLL SAIKSPCQRE TPEGAEAKPW YEPIYLGGVF 201        211        221        231
REF  QLEKGDRLSA EINRPDYLDF AESGQVYFGI IAL (SEQ ID NO: 2)
SEQ3 QLEKGDRLSA EINRPDYLDF DDDGQVYFGI IAL (SEQ ID NO: 3)
```

Polypeptides can be formed from at least two monomers that are couple directly or via an intermediate linker. When the polypeptide consists of three monomers, with or without intermediate linkers, it is referred to as a trimer. When the monomers are identical sequences, it is a homotrimer. When at least one of the monomers is different from another of the monomers, i.e., less than 100% identify between the two monomers, it is a heterotrimer. A trimer may have other sequences, for example a biotin, attached to one or both ends of the three connected monomers. In certain embodiments, the trimer has a binding group selected to bind to the substrate attached to one end. In certain embodiments, the binding group is selected to form an Schiff base bond with the substrate in the presence of an amine.

Table 6 lists an exemplary SEQ11 (SEQ ID NO:5) that is a modified TNF homotrimer. In certain embodiments, the modified sequence comprises two or more copies of a modified sequence. In certain embodiments, the trimer modified sequence comprises a linker, for example the string "GGGS" (SEQ ID NO:4) or multiples thereof, between copies of the modified TNF. In this example, three copies of the SEQ3 are coupled into a single chain trimer by linkers, wherein each linker is 4 copies of "GGGS," (SEQ ID NO:4) shown underlined. Additional sequences can be added at each end of the trimer, as indicated by the italicized letters "**xxxx".

TABLE 6

SEQ11 modified single chain TNF (scTNF) sequence

*THHHHH HHHHHAGGAE NLYFQGSASS*
SSRTPSDKPV AHVVANPQAE GQLQWVNRRA NALLANGVEL RDNQLVVPSE
GLYLIYSQVL FKGQGCPSTH VLLTHTISRI AVSYQTKVNL LSAIKSPCQR
ETPEGAEAKP WYEPIYLGGV FQLEKGDRLS AEINRPDYLD F<u>DDD</u>GQVYFG
IIALGGGSGG GSGGGSGGGS SSRTPSDKPV AHVVANPQAE GQLQWVNRRA
NALLANGVEL RDNQLVVPSE GLYLIYSQVL FKGQGCPSTH VLLTHTISRI
AVSYQTKVNL LSAIKSPCQR ETPEGAEAKP WYEPIYLGGV FQLEKGDRLS
AEINRPDYLD F<u>DDD</u>GQVYFG IIALGGGSGG GSGGGSGGGS SSRTPSDKPV
AHVVANPQAE GQLQWVNRRA NALLANGVEL RDNQLVVPSE GLYLIYSQVL
FKGQGCPSTH VLLTHTISRI AVSYQTKVNL LSAIKSPCQR ETPEGAEAKP
WYEPIYLGGV FQLEKGDRLS AEINRPDYLD F<u>DDD</u>GQVYFG UAL (SEQ
ID NO: 5) *\*\*xxxx*

The SEQ11 protein was expressed in *E coli* and purified to 80% purity by an immobilized metal chelate affinity chromatography (IMAC) column. The SEQ11 protein was coupled to agarose beads at densities of 1 mg/ml and 2 mg/ml of ligand per bead volume. Human plasma with TNF-R1 and TNF-R2 was passed through each of the columns and the residual amounts of the receptors was measured and compared to the original amount in the plasma.

Figure 1:
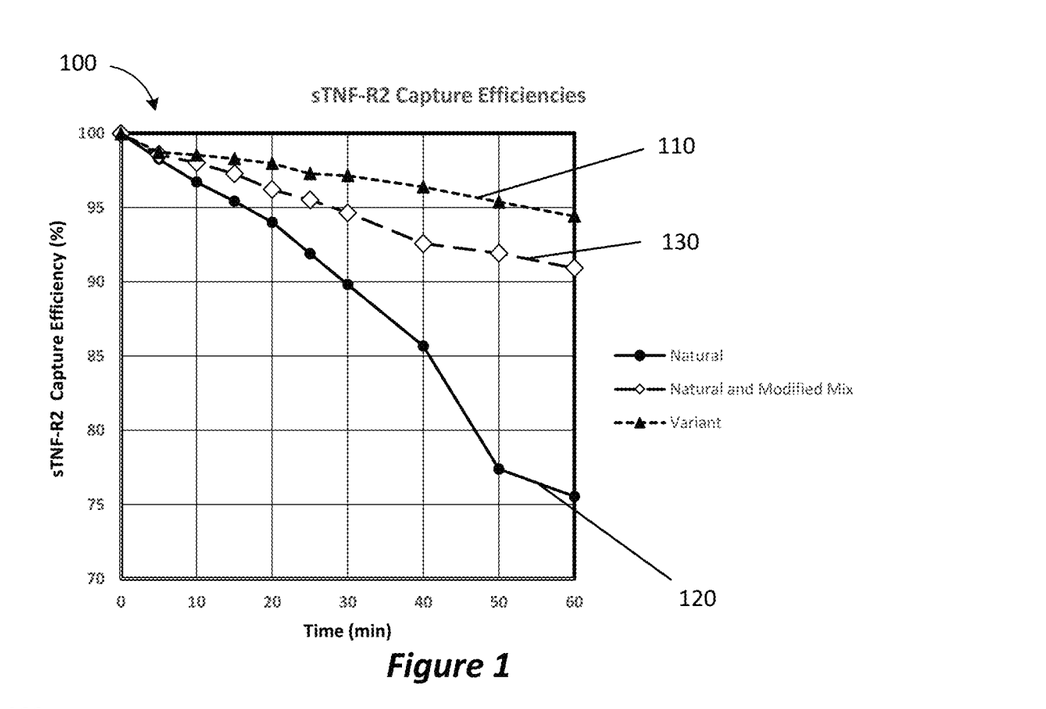
FIG. 1 is a plot of capture efficiency of sTNF-R2 removed from a test solution that was passed through experimental columns, according to certain aspects of the present disclosure.

FIG. 1 is a plot of capture efficiency of sTNF-R2 for various columns, according to certain aspects of the present disclosure. Full-size columns (15 ml) were prepared with three capture ligands:
 natural TNF trimer
 TNF variant trimer (SEQ11)
 a combination of natural TNF trimer and TNF variant trimer SEQ11

For the natural TNF and TNF variant columns, the beads were coated with approximately 1 mg of capture ligand per milliliter of beads (1 mg/ml density). The beads for the mixture column were coated with 1 mg of each capture ligand (natural and variant). The ratio of the variant TNF and natural TNF can be adjusted to determine the relative amounts of sTNF-R1 and sTNF-R2 that are removed from the blood component that passes through the column. In certain embodiments, the ratio is selected to remove more sTNF-R2 than would be removed by the natural TNF capture ligand alone. In certain embodiments, the ratio is adjusted to remove more sTNF-R2 than sTNF-R1. In certain embodiments, the ratio is adjusted to remove approximately the same amounts of sTNF-R2 and sTNF-R1. In certain embodiments, the ratio is adjusted to remove less sTNF-R2 than sTNF-R1.

A test solution was prepared using phosphate-buffered saline (PBS) with 0.025% bovine serum albumin (BSA). TNF-R1 added to reach 10 mg/ml and TNF-R2 is added to a level of 40 ng/ml. The solution has a pH=7.4. Experiments were run for 60 minutes at 30 ml/min, producing 1800 ml of effluent. The amount of sTNF-R2 in each sample was measured and the capture efficiency determined by comparison to the amount of sTNF-R2 in the original solution. Curve 120 shows that the capture efficiency of the natural TNF capture ligand drops away, being reduced to approximately 76% in 60 minutes. In comparison, curve 110 for the variant SEQ11 is still approximately 94% after 60 minutes. Curve 130 for the mixture of natural TNF and variant TNF shows a small drop, compared to curve 110, but is still above 90% after 60 minutes.

Figure 2:
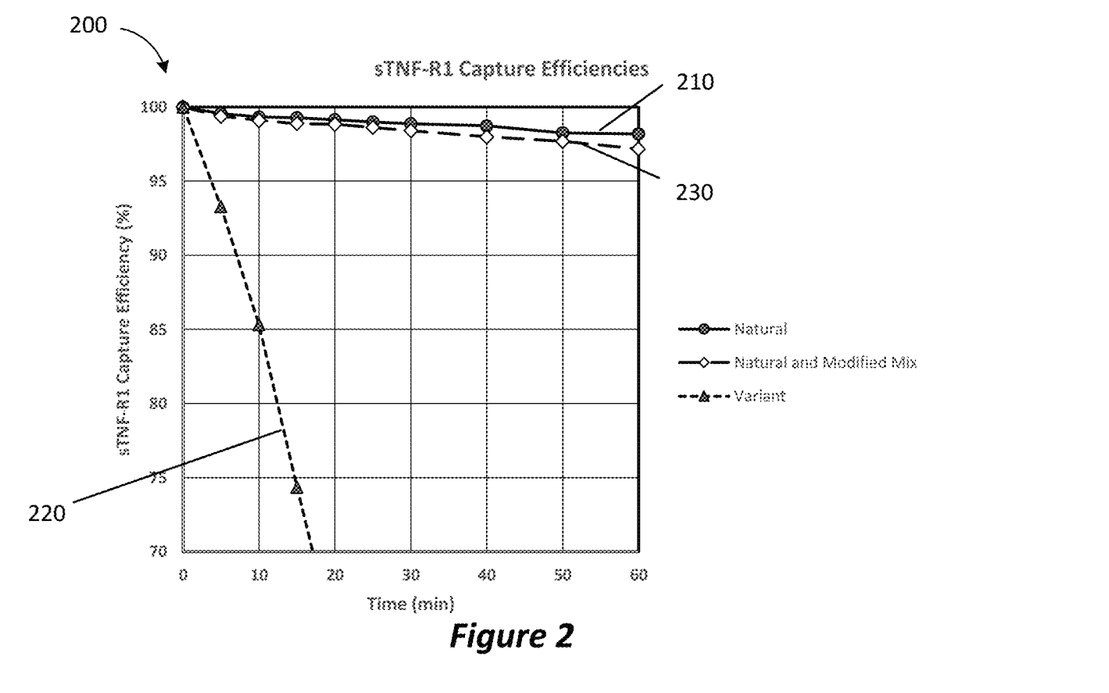
FIG. 2 is a plot of capture efficiency of sTNF-R1 removed from a test solution that was passed through experimental columns, according to certain aspects of the present disclosure.

FIG. 2 is a plot 200 of capture efficiency of sTNF-R1 for various columns, according to certain aspects of the present disclosure. Curve 210 for the natural TNF trimer remains high and is approximately 98% after 60 minutes. Curve 220 shows that the capture efficiency of the variant TNF capture ligand drops away quickly, however, and is below 70% in under 20 minutes. Curve 230 for the mixture of natural TNF and variant TNF shows a small drop, compared to curve 210, but is still above 95% after 60 minutes.

Figure 3:
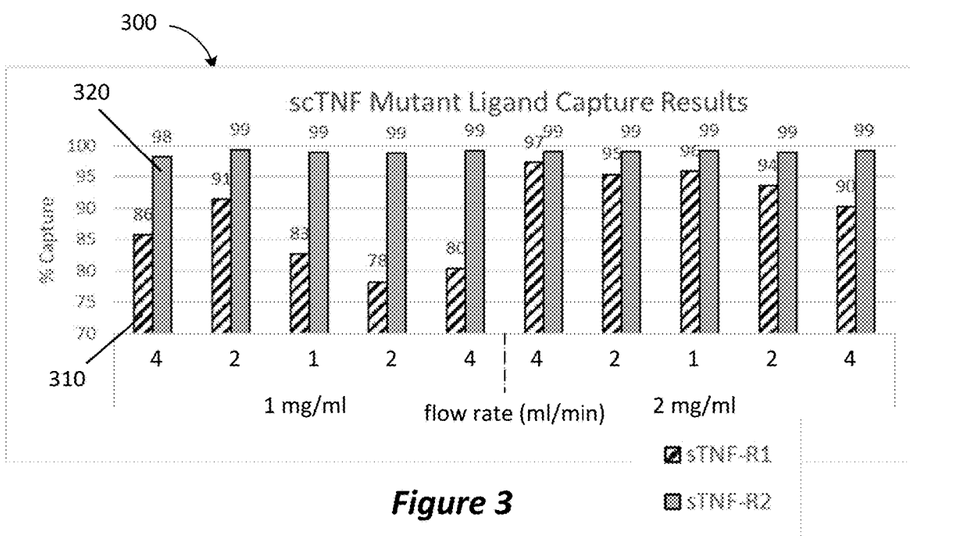
FIG. 3 is a plot of capture efficiency test measurements for different densities of capture ligand, according to certain aspects of the present disclosure.

FIG. 3 is a plot 300 of capture efficiency test measurements for different densities of the TNF variant capture ligand, according to certain aspects of the present disclosure. Test columns (1 ml capacity) were prepared at 1 mg/ml ligand density and at 2 mg/ml ligand density. A test fluid spiked with sTNF-R1 and sTNF-R2 was run through the columns at various rates, as indicated in the horizontal axis (sequentially 4, 2, 1, 2, and 4 ml/min). The data for the 1 mg/ml column is presented on the left, the 2 mg/ml column on the right. Samples were collected for 1 minute at each flow rate and analyzed. The striped bars 310 indicate the amount of sTNF-R1 captured and the solid bars indicate the amount of sTNF-R2 captured. It can be seen that 1 mg/ml density is sufficient to maintain a 98-99% capture efficiency for sTNF-R2 over the duration of this test and is not significantly improved by increasing the density to 2 mg/ml. The capture efficiency for sTNF-R1 was significantly improved from the 78-91% range to 97% initially, although it drops to 90% by the 5$^{th}$ sample. The average capture efficiency is summarized in Table 7.

TABLE 7

Capture Efficiency

Average Capture Efficiency

| Ligand Density | sTNF-R1 | sTNF-R2 |
|---|---|---|
| 1 mg/ml | 84% | 99% |
| 2 mg/ml | 94% | 99% |

Binding Affinity

The binding strength of the binding of a ligand and its target is characterized as the "equilibrium dissociation constant," or "$K_D$," that is the value obtained in a titration measurement at equilibrium, or by dividing the dissociation rate constant ($k_{off}$) by the association rate constant ($k_{on}$). Methods for determining association and dissociation rate constants are known in the art. The $K_D$ represents the inverse of the affinity of a ligand for a receptor, such that a smaller $K_D$ value is indicative of a higher binding affinity between a ligand and a receptor.

In certain embodiments, these methods may be used for comparing the binding affinities of various ligands for their targets. In one embodiment, the affinity of a TNF monomer ligand for a soluble TNF receptor is measured. In certain embodiments, the affinity of a native TNF molecule for binding to a soluble TNF receptor is compared to the affinity of a modified TNF molecule for binding to a soluble TNF receptor.

The experimentally measured affinity kinetics for native TNF and a modified TNF adsorbent were measured and the results provided in Table 8. Ligand affinities can be measured directly as a dissociation constant ($K_D$) that is measured in nanomolar (nM), wherein a lower $K_D$ is associated with higher binding affinity. The native TNF has over 10× higher affinity for sTNF-R1 than the modified version. The modified TNF, in contrast, shows increased affinity for sTNF-R2 compared to the native TNF.

TABLE 8

Affinity Measurements for binding of TNF polypeptides to sTNF-Rs

Equilibrium $K_D$

| | sTNF-R1 | sTNF-R2 |
|---|---|---|
| natural TNF | $K_D$ = 9 nM | $K_D$ = 18 nM |
| modified TNF | $K_D$ = 100 nM | $K_D$ = 12 nM |

In the context of the present disclosure, "increased" affinity of a ligand refers to a relative improvement in affinity (i.e., a lower measured $K_D$) during interactions with a soluble TNF receptor when compared to another ligand or when comparing its affinity for different soluble TNF receptors.

In certain embodiments, a modified TNF ligand has a $K_D$ for binding to sTNF-R2 that is less than the $K_D$ of a natural TNF ligand. In certain embodiments, a modified TNF ligand has a $K_D$ for binding to sTNF-R2 that is at least 10%, at least 20%, at least 25%, at least 30%, at least 50%, at least 100%, or at least 200% less than the $K_D$ of a natural TNF ligand.

Leaching

Leaching of the adsorbent is a known, and generally undesirable, characteristic of apheresis columns. The capture ligand dissociates from the substrate over a period of time as a blood component is flowed through the column. A leaching rate is often determined by the amount of ligand detected in the outflow of column. An initial leaching rate is the leaching rate measured after first contact of a ligand with a blood product for a predetermined initial period of time (e.g., 1 to 10 minutes) at a predetermined flow rate (e.g., 10 ml/minute). In certain embodiments, the initial leaching rate is higher than the leaching rate of the remainder of the treatment duration and the leaching rate of a column is characterized by the measured leaching rate at a predetermined flow rate after the initial time period has elapsed.

Table 8 reports the measurements taken at various steps of the process. The total collected volume was passed through a molecular-cutoff filter and the volume of the filtrate was measured. The concentration of TNF in the filtrate sample was then measured and scaled up to the total volume of 1800 ml to determine the total amount of TNF in the total volume (and converted from pg to ng). As the test ran for 1 hour, the leaching rate (in ng/min) is determined by the total amount of TNF in the effluent divided by 60 minutes.

TABLE 8

| average leaching rate | | | | | | |
|---|---|---|---|---|---|---|
| Capture ligand | Vol of filtrate | Cone of filtrate (pg/ml) | Total volume collected | Total pg in total volume | Total ng in total volume | Leaching rate (ng/min) |
| Modified TNF | 0.72 | 69 | 1800 | 124000 | 124 | 2.1 |
| Mixture | 0.38 | 33 | 1800 | 59400 | 59 | 1.0 |
| Natural TNF | 1.52 | 42 | 1800 | 75600 | 76 | 1.3 |

The maximum tolerated dose (MTD) of native TNF has been estimated to be 300 μg/$m^2$. As the body surface area (BSA) averages are 1.6 $m^2$ for women and 1.9 $m^2$ for men, an estimated total MTD is in the 4.8-5.7 μg range. It is desirable that the total TNF released by an apheresis column over the course of a treatment is less, and desirably much less, than this MTD. It has been reported that certain modified TNF molecules are less toxic than natural TNF.

For an example of a 2-hour apheresis treatment, a leaching rate of 2.1 ng/min (for the Modified TNF column of Table 8) will introduce approximately 252 ng of modified TNF in the patient. This is equivalent to a total dose from this treatment of approximately 0.25 μg, which is approximately 20× lower than the MTD estimated above.

In certain embodiments, a column is disclosed that has a leaching rate of less than or equal to 50 ng/min, less than or equal to 10 ng/min, less than or equal to 5 ng/min, less than or equal to 3 ng/min, less than or equal to 2 ng/min, or less than or equal to 1 ng/min.

Apheresis Column

FIG. 4 depicts an exemplary apheresis column 400 according to certain aspects of the present disclosure. The column 400 comprises a body 410 that comprises a compartment 420 having an inlet 430 and an outlet 434. In the example of FIG. 2, the compartment 420 is generally a right cylinder wherein the inlet 430 and outlet 434 are both planar circular disks. In certain embodiments, the cross-sectional shape of the compartment 420 may be oval, rectangular, or other regular or irregular or nonplanar geometric shape. In certain embodiments, the size and shape of one or both of the inlet 430 and outlet 434 may be different from the size and shape of the nominal cross-section of the compartment 420. In certain embodiments, fluid enters an entrance port 432 and is conveyed to the inlet 430. Similarly, in certain embodiments, fluid coming out of the outlet 434 is conveyed to an exit port 436. In use, the column may be oriented in any direction, including upside down, such that the direction of gravity in FIG. 4 may be in any direction.

Figure 4:
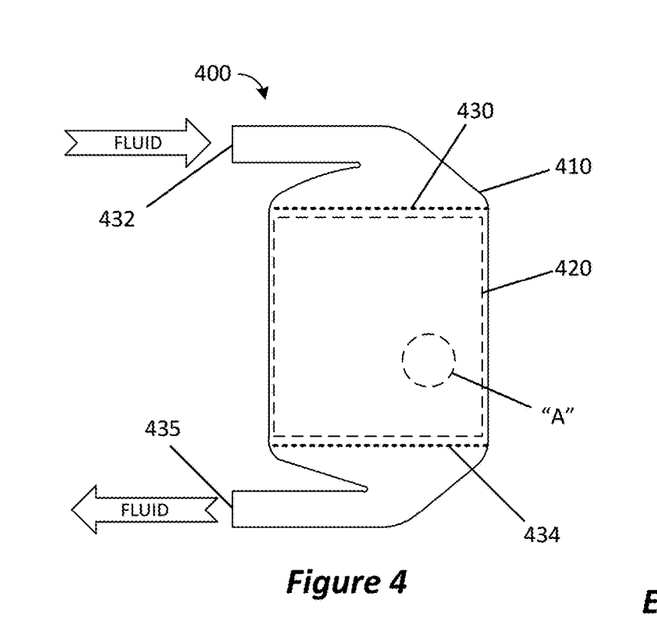
FIG. 4 depicts an exemplary apheresis column, according to certain aspects of the present disclosure.

In certain embodiments, one or both of the inlet 430 and outlet 434 comprise a porous wafer, commonly referred to as a "frit," that is fabricated by melting polyethylene beads together. The diameter of the beads and the degree of compression are chosen to produce an average pore size. In certain embodiments, the average pore size is 20 microns. In certain embodiments, the frit is formed by sintering beads comprising a metal or a ceramic, with the same effect. It is generally desirable to select an average pore size for the frit that allows the largest elements present in the incoming fluid to pass through the inlet 430 and outlet 434, thereby avoiding clogging of the column 400. It is further desirable to select the average pore size to retain the substrates, such as the beads 450 of FIG. 5, within the compartment 420.

Figure 5:
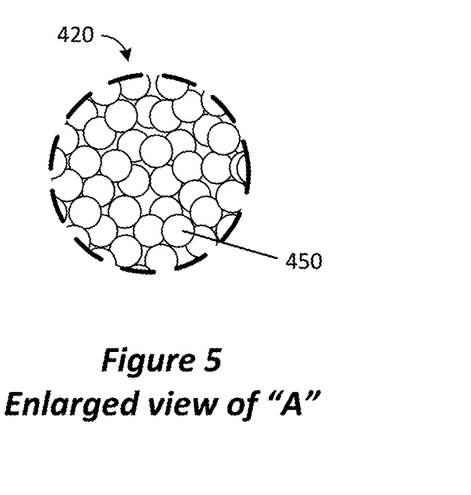
FIG. 5 depicts an enlarged view of an exemplary portion of the apheresis column of FIG. 4, according to certain aspects of the present disclosure.

FIG. 5 depicts an enlarged view of an exemplary portion "A" of the apheresis column 400 of FIG. 4, according to certain aspects of the present disclosure. In certain embodiments, the compartment 420 is at least partially filled with a substrate, for example a plurality of beads 450 as shown in FIG. 5. In certain embodiments, the beads 450 are spherical with a diameter in a range of 10-10000 microns, 20-1000 microns, 30-500 microns, 40-250 microns, 45-165 microns, 75-125 microns, or other ranges of diameters. In certain embodiments, the beads 750 have a common nominal diameter of 25, 50, 75, 100, 125, or 150 microns or other nominal diameter. In certain embodiments, the beads 450 are comprise a plurality of nominal diameters.

Figure 6:
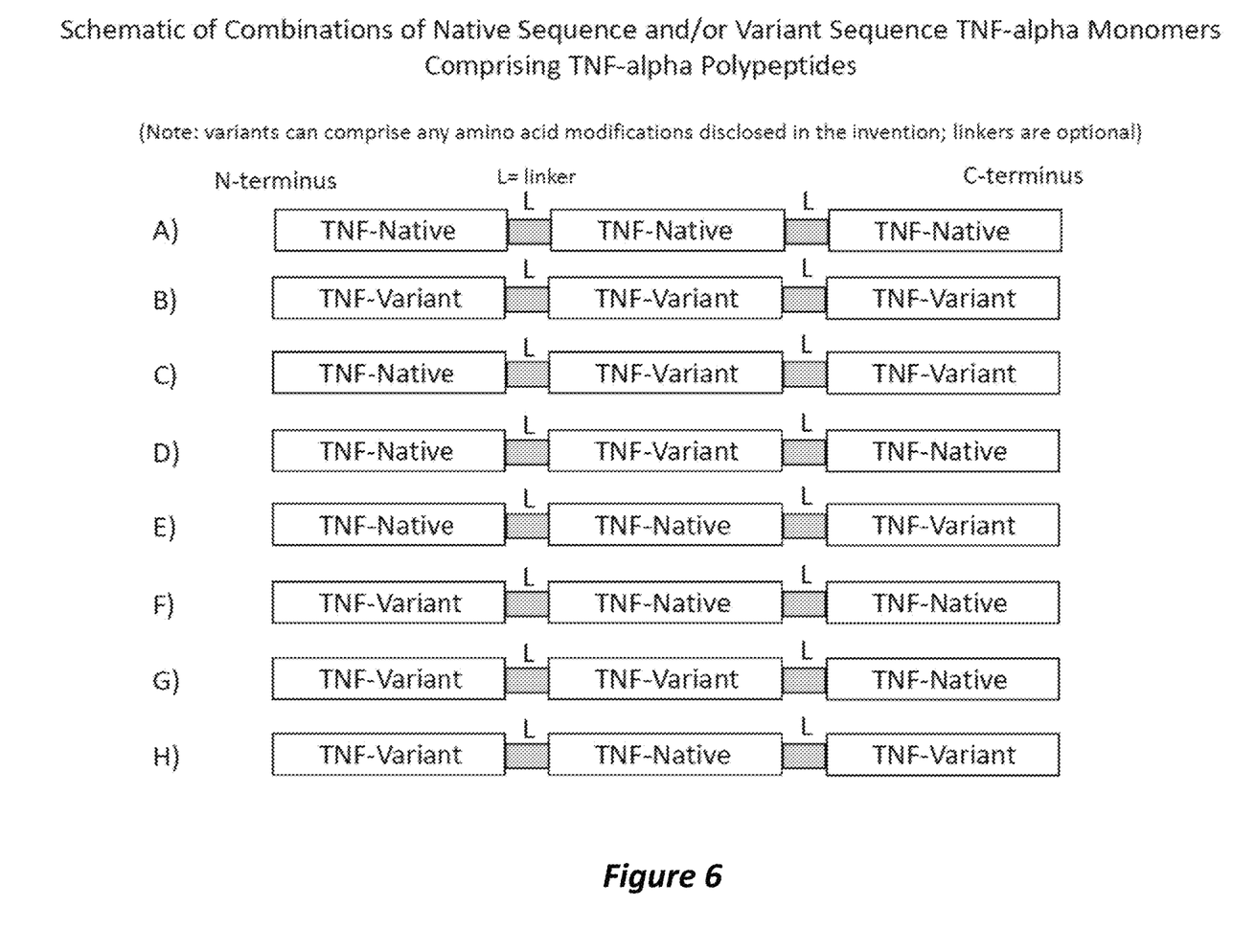
FIG. 6 illustrates nonlimiting exemplary embodiments of combinations of native TNF and modified (variant) TNF trimers with optional linkers.

FIG. 6 illustrates nonlimiting exemplary embodiments of combinations of native TNF and modified (variant) TNF trimers with optional linkers. In certain embodiments, a capture ligand comprises a plurality of trimers selected from the group of A-H of FIG. 6. In certain embodiments, the plurality of trimers are coupled separately to the substrate. In certain embodiments, the capture ligand is a homotrimer of either natural TNF monomers or modified TNF monomers. In certain embodiments, the capture ligand is a heterotrimer having both natural and modified TNF monomers. In certain embodiments, the trimer comprises a linker between at least one pair of the monomers. In certain embodiments, the trimer does not include any linkers between the monomers.

Methods of Treatment

The methods disclosed herein are useful for immune modulation for a patient with cancer or another disease condition including, but not limited to, autoimmune and inflammatory disorders. In certain embodiments, extracorporeal removal of a soluble TNF receptor from the blood or a blood component of a patient using immunoadsorptive means is provided for the treatment of a disease or condition. In certain embodiments, the disclosed methods are used for the treatment of hyperproliferative disorders, e.g., through the induction of apoptosis of immune cells using the methods disclosed herein. In certain embodiments, the disclosed methods are used for the treatment of infectious diseases, e.g., bacterial, viral, or protozoan infections. In certain embodiments, the disclosed methods are performed for the treatment of cancer, e.g., in a patient with a solid tumor or a hematologic malignancy.

The disclosed methods are based on the knowledge that soluble TNF receptors are released in high levels during some disease. Various diseases and medical conditions are associated with elevated levels of soluble TNF receptors in blood specimens (e.g., in serum or plasma) as compared to the levels of soluble TNF receptors found in a healthy individual. The concentrations of sTNF-R1 and sTNF-R2 in serum or plasma can be measured using methods known in the art, e.g., a Meso Scale Discovery (MSD) assay or ELISA.

In certain embodiments, extracorporeal manipulation, depletion and/or removal of soluble TNF receptors is performed, and the treated blood or blood fractions that have been partially depleted of soluble TNF receptors are returned to the patient. To perform such a procedure, peripheral blood is removed from a patient, anticoagulant agents are optionally added to the blood, and the blood is separated into its major components, for example, the separation of blood cells from a liquid component, e.g., plasma, may be performed using the apheresis machine. The liquid component is then preferably processed in a secondary circuit comprising a column as disclosed herein for the removal of a soluble TNF receptor. In certain embodiments, the column is configured to be fluidically coupled to apheresis machine tubing sets, intravenous tubing extension sets, fluidic tubing adapters, filters, stopcocks, and/or other elements commonly used in closed-loop patient fluid line assemblies. In certain embodiments, the column is configured such that the liquid component flows through system at a flow rate of between about 10 ml/min and about 100 ml/min. In certain embodiments, the flow rate is between about 20 ml/min and about 60 ml/min. In certain embodiments, the flow rate is between about 25 ml/min and about 50 ml/min. In certain embodiments, the flow rate is between about 30 ml/min and about 45 ml/min. In certain embodiments, a flow rate is selected to maintain a determined level of capture efficiency of the column for sTNF-R1 and/or sTNF-R2.

In certain embodiments, the fluid component is contacted with the ligand for a time that is sufficient to enable a determined minimum level of binding of a portion of the sTNF-R1 and sTNF-R2 in the fluid component to the immobilized capture ligand in the column. In certain embodiments, the column removes portions of both the sTNF-R1 and the sTNF-R2 in the fluid component.

In certain embodiments, a patient is selected for therapy using a method or system disclosed herein based on the quantities or concentrations of a soluble TNF receptor present in a blood specimen, e.g., as measured in a serum or plasma obtained from said patient prior to initiation of a method disclosed herein). In certain embodiments, a patient is selected for therapy using the methods disclosed herein based on threshold sTNF-R1 levels of at least 500 pg/ml, at least 750 pg/ml, at least 1,000 pg/ml, at least 1,500 pg/ml, or at least 2,000 pg/ml as measured in a blood specimen.

In certain embodiments, a patient is selected for therapy using a method or system disclosed herein based on threshold sTNF-R2 levels of at least 500 pg/ml, at least 750 pg/ml, at least 1,000 pg/ml, at least 1,500 pg/ml, at least 2,000 pg/ml, at least 5,000 pg/ml, or at least 10,000 pg/ml as measured in a blood specimen. In certain embodiments, therapy using a method or system disclosed herein is performed using columns comprising immobilized ligands that achieve a high capture efficiency for sTNF-R2. In certain embodiments, ligands that achieve a high capture efficiency for sTNF-R2 are selected from SEQ3-SEQ10.

In certain embodiments, a patient is selected for therapy using a method or system disclosed herein based on the TNF concentration that is quantified in a blood specimen. In certain embodiments, a threshold TNF concentration in the blood specimen is between 0.5 ng/ml and 5.0 ng/ml of TNF, between 0.5 ng/ml and 2.5 ng/ml, or between 2.5 ng/ml and 5 ng/ml. The concentration of TNF in a blood specimen can be measured using methods known in the art. In certain embodiments, the endogenous TNF level is measured prior to performing a method disclosed herein to define whether a threshold concentration of TNF is present in a blood component, e.g., a level of at least 0.5 ng/ml, at least 0.5 ng/ml, at least 1.0 ng/ml, at least 1.5 ng/ml, at least 2.0 ng/ml, at least 2.5 ng/ml, or at least 5.0 ng/ml. In certain embodiments, the concentration of TNF measured in a patient reflect the endogenous levels of TNF present in the plasma or serum of said patient. In certain embodiments, quantification of a concentration of TNF can be used to determine the likelihood that removal of a soluble TNF receptor (e.g., sTNF-R1, sTNF-R2, or both) will be impactful in improving the activity of TNF or treating a disease condition in a patient.

The In certain embodiments, the disclosed methods of treating a patient with an extracorporeal therapy are evaluated based on the capture efficiency of the columns utilized to perform the procedure. In certain embodiments. the clinical performance measures of the columns disclosed herein include sTNF-R1 and sTNF-R2 reductions from the total blood pool of a patient, e.g., measured by sampling peripheral blood. In certain embodiments. the clinical performance is defined by determination of the capture efficiency of the column, as measured by sampling the inflow concentrations of sTNF-R1 and sTNF-R2 in the body fluid being treated and the outflow concentrations of sTNF-R1 and sTNF-R2 at a particular time point during the apheresis procedure.

In certain embodiments of methods disclosed herein, samples of whole blood are collected from a patient's central line catheter during a single treatment of a patient at baseline (time=0 min), 30 min, 60 min, 90 min, and at the end of treatment (e.g., at the completion of 2 plasma volumes circulated through the system). In certain embodiments, other time intervals for collection of samples are used during a treatment. In certain embodiments, plasma samples are taken at approximately the same time at the inlet of a column and the outlet of a column for the measurement of capture efficiency of said column. In certain embodiments, whole blood and plasma samples are drawn at time intervals following cessation of the apheresis procedure, e.g., at 30 minutes, 60 minutes, 12 hours, 24 hours, 36 hours, and 48 hours post-treatment. The concentrations of sTNF-R1 and/or sTNF-R2 of collected samples of blood or blood components are measured using a quantitative assay. The differential between the concentrations of a particular soluble TNF receptor at the inlet of the column vs. the outlet is an indicator of the effectiveness of that column in capturing that soluble TNF receptor from the blood component.

In certain embodiments, the capture efficiency for one or both of sTNF-R1 and sTNF-R2 is at least 30%. In certain embodiments, the capture efficiency for one or both of sTNF-R1 and sTNF-R2 is at least 50%, at least 80%, at least 90%, at least 95%, at least 96%, at least 97%, at least 98%, at least 99%, or more.

In certain embodiments, a modified TNF has a higher affinity for a soluble TNF receptor than the affinity of the natural TNF for the same receptor. In certain embodiments, the relative capture efficiency of a column for sTNF-R1 and sTNF-R2 is determined by the relative amounts of natural TNF and modified TNF used as capture ligands in the column. In certain embodiments, the capture efficiency for a TNF receptor of a capture ligand comprising a trimer of modified TNF is greater than the capture efficiency for the same TNF receptor of a capture ligand comprising a trimer of natural TNF.

In certain embodiments, the capture efficiency of a column changes over time during the course of an apheresis procedure, e.g., after 5, 10, 15, 30, 45, 60, 90, 120, or 180 minutes of a treatment. For example, at least 70% of soluble TNF receptors in a blood sample may become bound to a ligand within a column within about 30 minutes. In certain embodiments, at least 80% or more of soluble TNF receptors in a flowing biological sample are bound to the capture ligand within a column within about 30 minutes. In certain embodiments, at least 90% or more of soluble TNF receptors in a flowing biological sample are bound to the capture ligand within a column within about 30 minutes. In certain embodiments, the disclosed column maintains a determined capture efficiency over a treatment time of 30 minutes, 45 minutes, 60 minutes, 120 minutes, or 180 minutes.

Although not wanting to be bound by any theory, the capture efficiency values described herein result from the use of the modified TNF molecules, and dimers, and trimers thereof described herein, in particular those having exceptionally high target affinity for sTNF-R2. In certain embodiments, the capture efficiency of a column for sTNF-R2 is improved by application of at least one modified TNF monomer comprising an amino acid substitution at a site selected from the group of sites 105, 221, 222, and 223 of the native sequence SEQ1. In certain embodiments, a capture efficiency is attained by application of at least one modified TNF monomer selected from SEQ3-SEQ10. In certain embodiments, a ligand comprising a modified TNF confers a capture efficiency of at least 30%, at least 50%, at least 70%, at least 80%, at least 90%, at least 95%, at least 96%, at least 97%, or at least 98% or more after approximately 30 minutes, approximately 45 minutes, approximately 60 minutes, approximately 120 minutes, or approximately 180 minutes of an apheresis procedure.

In certain embodiments, a capture ligand comprising a modified TNF monomer, dimer, or trimer described herein confers a capture efficiency of at least 30%, at least 50%, at least 70%, at least 80%, at least 90%, at least 95%, at least 96%, at least 97% or at least 98% or more after processing approximately one patient plasma volumes of body fluid, approximately 1.5 patient plasma volumes of body fluid, or approximately two patient plasma volumes of body fluid.

In certain embodiments, the total volume of a blood component to be treated using the methods disclosed herein, the total treatment times, and the frequency of administration of treatments are parameters are individualized for each patient. In certain embodiments, the total volume of plasma to be treated is one patient plasma volume. In certain embodiments, the total volume of plasma to be treated is two patient plasma volumes.

A formula for calculating total plasma volume $V_p$ (ml) is:

$$V_p = 0.065 \times W \times (1-\text{HCT})$$

wherein W is the patient weight (kg) and HCT is the hematocrit (%).

A formula for calculating patient treatment time T (min) based on the plasma volumes to be treated is:

$$T = (V_p \times V_x) \div Q$$

wherein $V_p$ is the patient plasma volume, $V_x$ is the number of patient plasma volumes to be treated, and Q is the flow rate (ml/min) of body fluid through the column. In certain embodiments, the patient treatment time is 1-4 hours in duration. In certain embodiments, the patient treatment time is 2-3 hours in duration.

In certain embodiments, methods are disclosed for determining the treatment times based on achievement of a specific target concentration reduction of sTNF-R1 or sTNF-R2 or both during an apheresis procedure. In certain embodiments, an apheresis procedure with a column having a first capture efficiency requires circulation of two patient plasma volumes through a column to achieve a specific target concentration reduction of the total quantities or the concentrations of sTNF-R1, sTNF-R2, or both from the patient's plasma. In certain embodiments an apheresis procedure with a column having a second capture efficiency that is twice than the first capture efficiency requires the circulation of one patient plasma volume through a column to achieve a comparable reduction in the total quantities or the concentrations of sTNF-R1, sTNF-R2 or both.

In some embodiments, a column disclosed herein is configured to remove at least 200 micrograms of a soluble TNF receptor (i.e., sTNF-R1 and/or sTNF-R2). In certain embodiments, a column comprises a modified TNF ligand. In preferred embodiments, a modified TNF ligand comprises a trimer. In certain embodiments a column disclosed herein is configured to remove between 50 micrograms and 250 micrograms of a soluble TNF receptor. For the purposes of illustration, an example patient has a concentration of soluble TNF receptors (combined sTNF-R1 and sTNF-R2) in the plasma in the range of 3-10 ng/ml and weighs 70 kg, wherein the patient plasma volume $V_p$ is approximately 50 ml per kg of body weight (W). The total amount R (ng) of a soluble TNF receptor in the patient is given by:

$$R = (V_p \times C) = ([50 \times W] \times C) = ([50 \times 70] \times [3-10])$$

$$R = 10500 - 35000 \text{ ng} = 10.5 - 35 \text{ micrograms}$$

There may also be other underlying factors, including disease-related variables, that affect the quantities of a soluble TNF receptor found in a blood component of a patient. For example, the total quantity of sTNF-R1 may range from 1-10 micrograms in the plasma of some patients and the total quantity of sTNF-R2 may range from 5-50 micrograms in the plasma of some patients. In certain embodiments, the quantities of soluble TNF receptors is estimated in a patient prior to administration of an extracorporeal therapy disclosed herein and/or following the administration of an extracorporeal therapy disclosed herein.

For effective removal of a soluble TNF receptor, plasma is contacted with the ligand for a time that is sufficient to allow binding and removal of a portion of a soluble TNF receptor. Subsequently, the plasma is recombined with the separated blood components and returned to the patient. In some embodiments, plasma is contacted with the ligand for a time that is sufficient to allow binding and removal of a portion of sTNF-R1 and sTNF-R2 from a blood component.

Aspects

A method is disclosed for reducing the concentration or quantity of sTNF-R2 in a blood component, the method comprising one or more of the steps:
(a) introducing blood or plasma comprising sTNF-R2 from a patient into an extracorporeal column comprising a modified TNF homotrimer that binds to said sTNF-R2;
(b) contacting the blood or plasma from the patient with the modified TNF ligand in the extracorporeal column for a time sufficient to allow the sTNF-R2 to bind to said modified TNF homotrimer;
(c) reintroducing the blood or plasma obtained after (b) into said patient, wherein the blood or plasma obtained after (b) has a reduced concentration or quantity of sTNF-R2 as compared to the blood or plasma of said patient prior to (b); and
(d) optionally, detecting or identifying the sTNF-R2 in a sample from said patient, such as a plasma or serum sample, prior to (a) or after (b) or both and/or optionally selecting or identifying a patient to receive a therapy that reduces the concentration or quantity of sTNF-R2.

A method is disclosed for reducing the concentrations or quantities of sTNF-R1 and sTNF-R2 in a blood component, the method comprising one or more of the steps:
(a) introducing blood or plasma comprising sTNF-R1 and sTNF-R2 from a patient into an extracorporeal column comprising a first ligand and a second ligand, wherein a first ligand comprises a native-sequence TNF homotrimer and a second ligand comprises a modified TNF homotrimer;
(b) contacting the blood or plasma from the patient with the first ligand, wherein the capture efficiency for sTNF-R1 is at least 80%;
(c) contacting the blood or plasma from the patient with the second ligand, wherein the capture efficiency for sTNF-R2 is at least 80%;
(d) reintroducing the blood or plasma obtained after (b) and (c) into said patient, wherein the blood or plasma obtained after (b) and (c) has a reduced concentration or quantity of sTNF-R1 and sTNF-R2 as compared to the blood or plasma of said patient prior to (b) and (c).

A method is disclosed of treating or inhibiting cancer in a patient, the method comprising one or more of the steps:
(a) optionally separating a blood fraction from the blood;
(b) removing a portion of the blood or blood fraction expressing a soluble TNF receptor using a first ligand coupled to a substrate, wherein the first ligand comprises a modified TNF monomer or a functional fragment thereof;
(c) removing a portion of the blood or blood fraction expression a soluble TNF receptor to a second ligand coupled to a substrate, wherein the second ligand comprises a native TNF monomer or a functional fragment thereof;
(d) reintroducing the blood or blood fraction after (b) and (c) into said patient, wherein the blood or blood fraction obtained after (b) and (c) has a reduced amount of a soluble TNF receptor as compared to the blood or blood fraction of said patient prior to (b) and (c); and (e) optionally, measuring the level or amount of a soluble TNF receptor in a sample from said patient, prior to (b) and (c) or after (b) and (c) or both.

A column is disclosed that has one or more performance specifications selected from the group consisting of:
(a) Biological safety: demonstrated to be biologically safe for use as an extracorporeal device supporting prolonged exposure to circulating blood;
(b) Target: sTNF-R1 and sTNF-R2;
(c) Capture efficiency: >80% for sTNF-R1 and sTNF-R2 following 30 minutes of treatment at a flow rate of 10-100, 20-60, 25-50, or 30-45 ml/min;

(d) Capture capacity: >200 µg of sTNF-Rs (sTNF-R1 plus sTNF-R2);
(e) Flow rate thru column: <60 ml/min;
(f) Treatment time: approximately 2 hours;
(g) Treatment volume: 2 patient plasma volumes;
(h) Leaching rate of capture ligand <50 ng/min.

A method is disclosed of treating or inhibiting cancer in a patient, the method comprising one or more of the steps:
(a) optionally separating a blood fraction from the blood;
(b) removing a portion of the blood or blood fraction expressing a soluble TNF receptor using a first ligand coupled to a substrate, wherein the first ligand comprises a modified TNF monomer or a functional fragment thereof;
(c) removing a portion of the blood or blood fraction expression a soluble TNF receptor to a second ligand coupled to a substrate, wherein the second ligand comprises a native TNF monomer or a functional fragment thereof;
(d) reintroducing the blood or blood fraction after (b) and (c) into said patient, wherein the blood or blood fraction obtained after (b) and (c) has a reduced amount of a soluble TNF receptor as compared to the blood or blood fraction of said patient prior to (b) and (c); and
(e) optionally, measuring the level or amount of a soluble TNF receptor in a sample from the patient prior to (b) and (c) and/or after (b) and (c).

In certain embodiments, a first ligand has a higher capture efficiency for either sTNF-R1 or sTNF-R2. In certain embodiments, a second ligand has a higher capture efficiency for either sTNF-R1 or sTNF-R. In certain embodiments, the capture efficiency of a first ligand for a soluble TNF receptor is at least 30%, at least 40%, at least 50%, at least 60%, at least 70% or at least 80%. In certain embodiments, the capture efficiency of a second ligand for a soluble TNF receptor is at least 30%, at least 40%, at least 50%, at least 60%, at least 70% or at least 80%.

In summary, modified TNF exhibits an increased affinity for sTNF-R2, compared to natural TNF. Furthermore, inclusion of both natural TNF and modified TNF in a column shows effective levels of removal for both sTNF-R1 and sTNF-R2.

Headings and subheadings, if any, are used for convenience only and do not limit the invention.

All applications, publications, patents and other references, GenBank citations and ATCC citations cited herein are incorporated by reference in their entirety. In case of conflict, the specification, including definitions, will control.

All of the features disclosed herein may be combined in any combination. Each feature disclosed in the specification may be replaced by an alternative feature serving a same, equivalent, or similar purpose. Thus, unless expressly stated otherwise, disclosed features (e.g., ligand (e.g., native or modified TNF), column, substrate, compartment are an example of a genus of equivalent or similar features.

As used herein, all numerical values or numerical ranges include integers within such ranges and fractions of the values or the integers within ranges unless the context clearly indicates otherwise. Thus, to illustrate, reference to a $K_D$ in a range of about $1\times10^{-6}$-$1\times10^{-9}$, $1\times10^{-6}$-$1\times10^{-8}$, $1\times10^{-6}$-$1\times10^{-7}$, $1\times10^{-7}$-$1\times10^{-9}$, $1\times10^{-7}$-$1\times10^{-8}$, or $1\times10^{-8}$-$1\times10^{-9}$ M (mol/liter) includes a range of $2\times10^{-6}$-$1\times10^{-9}$, $2\times10^{-6}$-$1\times10^{-8}$, $2\times10^{-6}$-$1\times10^{-7}$, $2\times10^{-7}$-$1\times10^{-9}$, $2\times10^{-7}$-$1\times10^{-8}$, $2\times10^{-8}$-$1\times10^{-9}$ M (mol/liter) and includes a range of $3\times10^{-6}$-$1\times10^{-9}$, $3\times10^{-6}$-$1\times10^{-8}$, $3\times10^{-6}$-$1\times10^{-7}$, $3\times10^{-7}$-$1\times10^{-9}$, $3\times10^{-7}$-$1\times10^{-8}$, $3\times10^{-8}$-$1\times10^{-9}$ M (mol/liter) and includes a range of $4\times10^{-6}$-$1\times10^{-9}$, $4\times10^{-6}$-$1\times10^{-8}$, $4\times10^{-6}$-$1\times10^{-7}$, $4\times10^{-7}$-$1\times10^{-9}$, $4\times10^{-7}$-$1\times10^{-8}$, $4\times10^{-8}$-$1\times10^{-9}$ M (mol/liter) and includes a range of $5\times10^{-6}$-$1\times10^{-9}$, $5\times10^{-6}$-$1\times10^{-8}$, $5\times10^{-6}$-$1\times10^{-7}$, $5\times10^{-7}$-$1\times10^{-9}$, $5\times10^{-7}$-$1\times10^{-8}$, $5\times10^{-8}$-$1\times10^{-9}$ M (mol/liter) and includes a range of $6\times10^{-6}$-$1\times10^{-9}$, $6\times10^{-6}$-$1\times10^{-8}$, $6\times10^{-6}$-$1\times10^{-7}$, $6\times10^{-7}$-$1\times10^{-9}$, $6\times10^{-7}$-$1\times10^{-8}$, $6\times10^{-8}$-$1\times10^{-9}$ M (mol/liter), etc.

Reference to an integer with more (greater, at least) or less than includes any number greater or less than the reference number, respectively. Thus, for example, reference to less than 100 includes 99, 98, 97, etc. all the way down to the number one (1); and less than 10 includes 9, 8, 7, 6, 5, 4 etc. all the way down to the number one (1).

As used herein, all numerical values or ranges include fractions of the values and integers within such ranges and fractions of the integers within such ranges unless the context clearly indicates otherwise. Thus, to illustrate, reference to a numerical range, such as $1\times10^{-6}$-$1\times10^{-9}$, $1\times10^{-6}$-$1\times10^{-8}$, $1\times10^{-6}$-$1\times10^{-7}$, $1\times10^{-7}$-$1\times10^{-9}$, $1\times10^{-7}$-$1\times10^{-8}$, and $1\times10^{-8}$-$1\times10^{-9}$ M (mol/liter) includes a range of $1.1\times10^{-6}$-$1\times10^{-9}$, $1.1\times10^{-6}$-$1\times10^{-8}$, $1.1\times10^{-6}$-$1\times10^{-7}$, $1.1\times10^{-7}$-$1\times10^{-9}$, $1.1\times10^{-7}$-$1\times10^{-8}$, and $1.1\times10^{-8}$-$1\times10^{-9}$ M (mol/liter), and includes a range of $1\times10^{-6}$-$0.9\times10^{-9}$, $1\times10^{-6}$-$0.9\times10^{-8}$, $1\times10^{-6}$-$0.9\times10^{-7}$, $1\times10^{-7}$-$0.9\times10$, $1\times10^{-7}$-$0.9\times10^{-8}$, and $1\times10^{-8}$-$0.9\times10^{-9}$ M (mol/liter), etc.

Reference to a series of ranges includes ranges which combine the values of the boundaries of different ranges within the series. Thus, to illustrate reference to a series of ranges, for example, 70%-80%, 70%-85%, 80%-90%, 90%-95% and 95%-98% includes, for example, 70%-90%, 70%-95%, 80%-85%, 80%-95%, 85%-90%, 85%-95% and 90%-98%.

Reference to an element in the singular is not intended to mean "one and only one" unless specifically so stated, but rather "one or more." Use of the articles "a" and "an" is to be interpreted as equivalent to the phrase "at least one." Unless specifically stated otherwise, the terms "a set" and "some" refer to one or more.

Terms such as "top," "bottom," "upper," "lower," "left," "right," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Moreover, nothing disclosed herein is intended to be dedicated to the public regardless of whether such disclosure is explicitly recited in the claims. A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such as an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

Although embodiments of the present disclosure have been described and illustrated in detail, it is to be clearly understood that the same is by way of illustration and example only and is not to be taken by way of limitation, the scope of the present invention being limited only by the terms of the appended claims.

What is claimed is:

1. A column for removal of a soluble tumor necrosis factor receptor 2 (sTNF-R2) from a body fluid, the column comprising:
 a compartment;
 an inlet coupled to the compartment and configured to receive the body fluid;
 a substrate disposed within the compartment; and
 a capture ligand coupled to the substrate and comprising a modified sequence comprising an amino acid substitution in a reference sequence that comprises a portion of a natural tumor necrosis factor (TNF) sequence;
 wherein the reference sequence is SEQ1 (SEQ ID NO: 1), and the modified sequence comprises an amino acid substituted at a site selected from a group consisting of sites 105, 221, 222, and 223 of SEQ1 (SEQ ID NO:1) and has an affinity for the sTNF-R2 that is greater than an affinity of the reference sequence for the sTNF-R2.

2. The column of claim 1, wherein the amino acid being substituted is selected from a group consisting of aspartic acid (D), glycine (G), histidine (H), asparagine (N), glutamine (Q), serine (S), threonine (T), and valine (V).

3. The column of claim 2, wherein the modified sequence comprises a substitution of D at one or more of sites 221, 222, and 223 of the reference sequence.

4. The column of claim 3, wherein the modified sequence comprises a substitution of D at two or more of sites 221, 222, and 223.

5. The column of claim 4, wherein the modified sequence comprises a substitution of D at all of sites 221, 222, and 223.

6. The column of claim 5, wherein the modified sequence comprises SEQ3 (SEQ ID NO:3).

7. The column of claim 1, wherein the capture ligand comprises at least two modified sequences.

8. The column of claim 7, wherein the capture ligand comprises a trimer of the modified sequence.

9. The column of claim 8, wherein the capture ligand comprises SEQ11 (SEQ ID NO:5).

10. The column of claim 7, wherein the capture ligand comprises a linker between the at least two modified sequences.

11. The column of claim 7, wherein the capture ligand does not comprise a linker.

12. The column of claim 1, wherein the capture ligand further comprises the reference sequence.

13. The column of claim 12, wherein the capture ligand comprises a first trimer of the modified sequence and a second trimer of the reference sequence, each of the first and second trimers coupled separately to the substrate.

14. The column of claim 12, wherein the capture ligand comprises a trimer comprising at least one of the modified sequences and at least one of the reference sequence.

15. The column of claim 12, wherein the column has a capture efficiency for the sTNF-R2 that is greater than 80% after 60 minutes of continuous operation at a flow rate of two column volumes per minute.

16. The column of claim 15, wherein the column has a capture efficiency for the sTNF-R2 that is greater than 90% after 60 minutes of continuous operation at a flow rate of two column volumes per minute.

17. The column of claim 1, wherein the modified sequence has an identity of 95% or greater with the reference sequence.

18. The column of claim 17, wherein the modified sequence has an identity of 98% or greater with the reference sequence.

19. The column of claim 17, wherein the modified sequence has an identity of 99.9% or less with the reference sequence.

20. The column of claim 1, wherein the modified sequence has a $K_D$ that is at least 10% less than a $K_D$ of the reference sequence.

21. The column of claim 20, wherein the modified sequence has a $K_D$ that is at least 30% less than a $K_D$ of the reference sequence.

* * * * *